United States Patent
Good et al.

(10) Patent No.: US 9,968,387 B2
(45) Date of Patent: May 15, 2018

(54) ROD INSERTER, SYSTEM AND METHOD

(71) Applicant: AESCULAP IMPLANT SYSTEMS, LLC, Center Valley, PA (US)

(72) Inventors: Chris Good, Center Valley, PA (US); Keith Christman, Center Valley, PA (US)

(73) Assignee: AESCULAP IMPLANT SYSTEMS, LLC, Center Valley, PA (US)

( * ) Notice: Subject to any disclaimer, the term of this patent is extended or adjusted under 35 U.S.C. 154(b) by 66 days.

(21) Appl. No.: 14/989,518

(22) Filed: Jan. 6, 2016

(65) Prior Publication Data
US 2017/0189084 A1    Jul. 6, 2017

(51) Int. Cl.
*A61B 17/70* (2006.01)
*A61B 17/00* (2006.01)

(52) U.S. Cl.
CPC ...... *A61B 17/7089* (2013.01); *A61B 17/7085* (2013.01); *A61B 2017/00367* (2013.01)

(58) Field of Classification Search
CPC ............ A61B 17/7083; A61B 17/7085; A61B 17/7086; A61B 17/7088; A61B 17/7089
See application file for complete search history.

(56) References Cited

U.S. PATENT DOCUMENTS

| | | | |
|---|---|---|---|
| 6,530,929 B1 | 3/2003 | Justis et al. | |
| 7,008,422 B2 | 3/2006 | Foley et al. | |
| 7,011,660 B2 | 3/2006 | Sherman et al. | |
| 7,077,372 B2 | 7/2006 | Moran | |
| 7,188,626 B2 | 3/2007 | Foley et al. | |
| 7,520,879 B2 | 4/2009 | Justis et al. | |
| 7,648,506 B2 | 1/2010 | McCord et al. | |
| 7,648,507 B2 | 1/2010 | Techiera et al. | |
| 7,686,809 B2 | 3/2010 | Triplett et al. | |
| 7,717,944 B2 | 5/2010 | Foley et al. | |
| 7,763,055 B2 | 7/2010 | Foley | |
| 7,862,595 B2 | 1/2011 | Foley et al. | |
| 7,867,259 B2 | 1/2011 | Foley et al. | |
| 7,871,424 B2 | 1/2011 | Abdelgany | |
| 7,922,727 B2 | 4/2011 | Songer et al. | |
| 8,038,699 B2 | 10/2011 | Cohen et al. | |
| 8,070,751 B2 | 12/2011 | Justis et al. | |
| 8,100,909 B2 | 1/2012 | Butler et al. | |

(Continued)

FOREIGN PATENT DOCUMENTS

| | | |
|---|---|---|
| EP | 1221901 A1 | 7/2002 |
| EP | 1221901 B1 | 2/2007 |

(Continued)

*Primary Examiner* — Julianna N Harvey
(74) *Attorney, Agent, or Firm* — Kenealy Vaidya LLP (57) ABSTRACT

A rod inserter, system and method are provided which allows for insertion of a rod through a freehand method. The inserter can include an extension structure extending from a handle, the extension structure having a distal end, a proximal end, and a longitudinal axis. The inserter can also include a plurality of linkage structures located in a passageway in the extension structure. The linkage structures can cause a rod connection structure to connect to the rod when the distal linkage structure is moved in a first direction, and to cause the rod connection structure to disconnect from the rod when the distal linkage structure is moved in a second direction substantially opposite to the first direction.

21 Claims, 7 Drawing Sheets

(56) References Cited

U.S. PATENT DOCUMENTS

| | | |
|---|---|---|
| 8,147,490 B2 | 4/2012 | Bauer |
| 8,182,509 B2 | 5/2012 | Abdelgany |
| 8,246,624 B2 | 8/2012 | Forton et al. |
| 8,343,160 B2 | 1/2013 | Techiera et al. |
| 8,361,124 B2 | 1/2013 | Sherman et al. |
| 8,721,685 B2 | 5/2014 | Foley et al. |
| 8,728,125 B2 | 5/2014 | Bruneau et al. |
| 8,900,275 B2 | 12/2014 | Justis et al. |
| 8,920,425 B2 | 12/2014 | Techiera et al. |
| 8,961,524 B2 | 2/2015 | Foley et al. |
| 2002/0161368 A1 | 10/2002 | Foley et al. |
| 2003/0060826 A1 | 3/2003 | Foley et al. |
| 2003/0229347 A1 | 12/2003 | Sherman et al. |
| 2005/0021031 A1 | 1/2005 | Foley et al. |
| 2005/0121576 A1 | 6/2005 | Moran |
| 2005/0131419 A1 | 6/2005 | McCord et al. |
| 2006/0111714 A1 | 5/2006 | Foley |
| 2006/0200135 A1 | 9/2006 | Sherman et al. |
| 2006/0229614 A1 | 10/2006 | Foley et al. |
| 2006/0265003 A1 | 11/2006 | Abdelgany |
| 2007/0049931 A1* | 3/2007 | Justis ................ A61B 17/7089 606/86 A |
| 2007/0185491 A1 | 8/2007 | Foley et al. |
| 2007/0198015 A1 | 8/2007 | Foley et al. |
| 2007/0213714 A1* | 9/2007 | Justis ................ A61B 17/7002 606/86 A |
| 2010/0094359 A1 | 4/2010 | Techiera et al. |
| 2010/0222828 A1* | 9/2010 | Stad ................ A61B 17/8891 606/86 A |
| 2010/0312279 A1 | 12/2010 | Gephart et al. |
| 2011/0071571 A1 | 3/2011 | Abdelgany |
| 2011/0106187 A1 | 5/2011 | Foley et al. |
| 2013/0012984 A1* | 1/2013 | Wall ................ A61B 17/7083 606/206 |
| 2013/0053834 A1 | 2/2013 | Meyer et al. |
| 2013/0072987 A1 | 3/2013 | Justis et al. |
| 2013/0096626 A1 | 4/2013 | Techiera et al. |
| 2013/0150905 A1 | 6/2013 | Karpowicz |
| 2014/0155941 A1 | 6/2014 | Foley et al. |
| 2014/0249592 A1* | 9/2014 | Black ................ A61B 17/7004 606/86 A |
| 2014/0257416 A1* | 9/2014 | Meyer ................ A61B 17/7089 606/86 A |
| 2014/0336709 A1 | 11/2014 | Avidano et al. |
| 2015/0045842 A1 | 2/2015 | Justis et al. |
| 2015/0245856 A1 | 9/2015 | Gephart et al. |

FOREIGN PATENT DOCUMENTS

| | | |
|---|---|---|
| EP | 2234550 A1 | 10/2010 |
| EP | 2277468 B1 | 3/2012 |
| EP | 1737366 B1 | 12/2012 |
| EP | 2234550 B1 | 9/2014 |
| WO | 2001028436 A1 | 4/2001 |
| WO | 2007090021 A1 | 8/2007 |
| WO | 2009083741 A1 | 7/2009 |

* cited by examiner

ROD INSERTER, SYSTEM AND METHOD

BACKGROUND

1. Field

The presently disclosed subject matter relates generally to surgical instrumentation devices, systems, and related methods, and more specifically to a rod inserter, system and method for use in placing, rearranging, and/or implanting a rod into a body, such as a spinal rod for placement adjacent to vertebrae of a spinal column.

2. Description of the Related Art

In order to stabilize the vertebrae of the spine, medical professionals have typically attached a stabilization rod along the spinal column using a series of pedicle screws attached to vertebrae. Each of the pedicle screws has a threaded portion and a head portion, with the threaded portion including screw threads that can grip each separate vertebrae. The head of the pedicle screw can include a saddle or U-shaped opening into which the spinal rod can be located. Also, set screws can be used to lock the spinal rod into the saddle or U-shaped portion of each of the pedicle screws. Of course, other shaped openings can be used on the pedicle screw for placement of the spinal rod.

During implantation or other manipulation of the spinal rod and system, a rod inserter is commonly used to insert the spinal rod into the opening(s) in the head of each pedicle screw. In general, alignment of the rod into each of the series of pedicle screws can be difficult to accomplish due to space requirements, variation in alignment of the pedicle screws, and the amount of force required to manipulate and/or bend the spinal rod. A rod inserter is often used to accomplish this task. There has been a longfelt need for the rod inserter to attach and detach quickly and securely to an end of the rod that is being implanted, while also providing a certain degree of movement and manipulation ability for the rod when the rod is secured to the rod inserter.

Conventional rod inserters have included devices that are bulky and have limited degrees of motion, while also requiring greater movement on the part of the operator to couple to a rod, such as a spinal rod, and to manipulate the spinal rod.

SUMMARY

Some surgeons prefer to use a freehand motion for rod insertion. Thus, there is a need for a freehand rod inserter that facilitates insertion of a rod with a minimal amount of damage to the skin, muscle and other tissues. Accordingly, it may be beneficial to provide a rod inserter device, system, and method for use by a surgeon using a freehand method, that: allows the rod to be held securely, preventing rotational and translational motions; allows for bending loads to be applied to the rod; and releases the rod only when the surgeon wishes the rod to be released. The rod inserter device, system and method according to the disclosed embodiments also requires minimal space, is easily and accurately operated, and is also easily dismantled for cleaning, inspection, etc.

The rod inserter can be used in surgery, for example, during placement of a rod adjacent a bone. In particular, the rod inserter can be used to implant a spinal rod for posterior fusion of the spine.

According to an aspect of the disclosed subject matter, the rod inserter can be helpful when fitting a spinal rod to a pedicle screw(s) in the spine, especially when the rod is difficult to place in the screw head. The difficulty of placing the rod in the screw head is quite common for long fusion cases where multiple polyaxial screws are joined in a row or series by one rod and especially when the screws are at slightly different heights relative to the bone in which they are inserted.

The streamlined shape of the rod inserter enables the rod inserter to be used without making a larger incision than is necessary to insert the rod. The inventive rod inserter of the instant application can therefore be used during less invasive operations which have been shown to reduce patient trauma. The rod inserter is designed for ease of use.

The rod inserter is designed to be cleanable by dismantling the various components after use. The rod inserter can also include several opening into and through which steam and/or cleaning fluids are easily penetrable.

According to one aspect, a rod inserter for use with a rod can include a handle, a curved extension structure extending from the handle, the extension structure having a distal end, a proximal end, and a longitudinal axis, the extension structure including a passageway extending along the longitudinal axis of the extension structure. A rod connection structure can be located at the distal end of the extension structure, the rod connection structure configured to connect and disconnect from the rod. A proximal linkage structure can be located in the passageway of the extension structure and adjacent the handle, and a distal linkage structure can be located in the passageway of the extension structure and adjacent the rod connection structure. Thus, the proximal linkage structure can be connected to the distal linkage structure, and the distal linkage structure can be configured to cause the rod connection structure to connect to the rod when the distal linkage structure is moved in a first direction, and to cause the rod connection structure to disconnect from the rod when the distal linkage structure is moved in a second direction substantially opposite to the first direction.

In accordance with yet another aspect of the disclosed subject matter a rod inserter can include a handle and an arcuate housing extending from the handle, the housing defining a passageway extending along a longitudinal axis of the housing. A plurality of links can be located in the passageway of the housing, at least one of the links extending in an arcuate manner along the longitudinal axis of the housing. A rod connection structure can be connected to at least one of the plurality of links and configured to connect to and release from a rod. An actuation structure can be connected via the plurality of links to the rod connection structure, the actuation structure configured such that actuation of the actuation structure causes the rod connection structure to connect to the rod and de-actuation of the actuation structure causes the rod connection structure to release from the rod.

In accordance with still another aspect of the disclosed subject matter, a method of using a rod inserter for inserting a rod can include providing a rod inserter including, a handle, an actuator located adjacent the handle, an extension structure extending from the handle, the extension structure having a distal end, and a proximal end, the extension structure including an passageway running along and defining a curved longitudinal axis of the extension structure, a plurality of links located in the passageway of the extension structure, and a rod connection structure located at the distal end of the extension structure, the rod connection structure configured to connect to and release from the rod. The method can further include actuating the actuator to move at least two of the plurality of links along the curved longitudinal axis of the extension structure, and actuating the actuator to cause the rod connection structure to one of connect to the rod and release from the rod.

BRIEF DESCRIPTION OF THE DRAWINGS

The disclosed subject matter of the present application will now be described in more detail with reference to exemplary embodiments of the apparatus, system and method, given by way of example, and with reference to the accompanying drawings, in which.

DETAILED DESCRIPTION OF EXEMPLARY EMBODIMENTS

A few inventive aspects of the disclosed embodiments are explained in detail below with reference to the various figures. Exemplary embodiments are described to illustrate the disclosed subject matter, not to limit its scope, which is defined by the claims. Those of ordinary skill in the art will recognize a number of equivalent variations of the various features provided in the description that follows.

Figure 1:
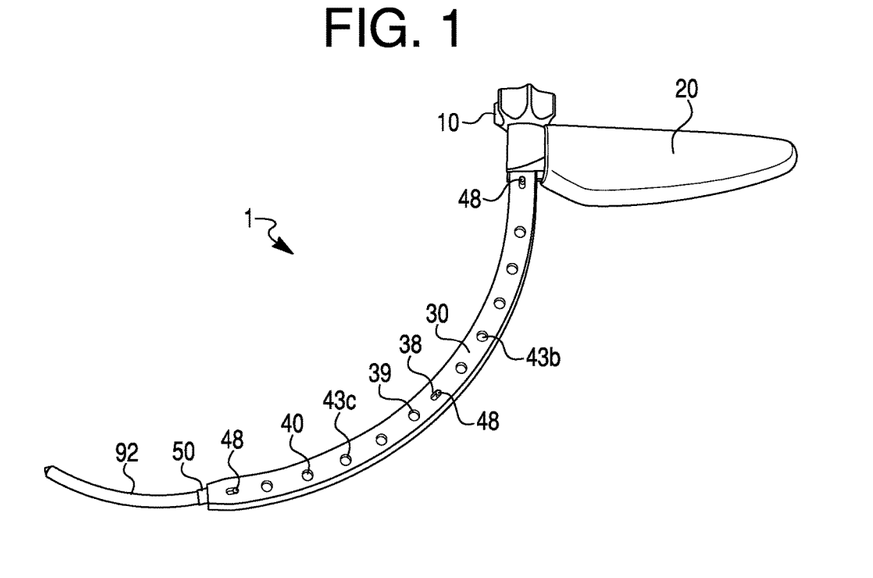
FIG. 1 is a perspective view of an example of a rod inserter device made in accordance with principles of the disclosed subject matter.

FIG. 1 illustrates an embodiment of a rod inserter 1 for inserting a rod 92 into a patient, made in accordance with principles of the disclosed subject matter. For example, the rod inserter 1 can be configured to be an instrument for use with the rod 92 in a rod-based pedicle screw system. The rod inserter 1 can include a handle 20, a housing 30, a link structure 40 and a rod connection structure, such as a collet 50. The rod inserter 1 can include an actuation structure configured in various forms, such as a knob 10, located adjacent the handle 20. In the present embodiment, the link structure 40 extends from a distal portion of the handle 20 through to a distal portion of the housing 30, and the knob 10 can be disposed at a proximal end of the housing 30 adjacent the handle 20. The link structure 40 can include links 43a-c, and can be configured to move as an inner shaft within the housing 30 via rotation of the knob 10 such that the link structure 40 moves relative to both the handle 20 and the housing.

The housing 30 of the present embodiment can be curved so as to assist with articulation of the rod inserter 1 by an operator into an incision in a patient, as described in more detail below. The curve of the housing 30 may (or may not) correspond to a similar curve in the rod 92 such that when connected to the rod inserter 1, the rod 92 forms an extension of the curve of the housing 30. The curve of the housing 30 in some embodiments may be of varying degree, and need not be the same or a similar curve to that of the rod 92. In this manner, the curve of the housing 30 is configured to allow for dynamic insertion of the rod 92 into the patient. In one embodiment, the radius of curvature of the housing 30 can be continuous along its entire length from the connection to the handle 20 to the distal most portion of the housing 30. In addition, the radius of curvature can be located above a top side of the housing (opposed to the direction in which the handle 20 extends from the housing 30), and can vary in degrees, as indicated above, and can be an arc of radius of 10 cm to 50 cm. Similarly, the longitudinal axis of extension structure and the distal linkage structure can both be continuously curved and can each have a radius of curvature located on a same side of the extension structure.

In the present embodiment, the housing 30 can include an aperture 38 through which a corresponding guide pin 48 of the link structure 40 may be viewed and/or extend. The guide pin 48 is configured to move substantially linearly within the aperture 38 to correspond with movement of the link structure 40 within the housing 30. Alternate embodiments of the rod inserter 1 may include any number of apertures 38 and corresponding guide pins, such as two, three, four, five, etc. Additionally, the housing 30 can have additional apertures 39 for cleaning and sterilization of the link structure 40 and the housing 30 of the rod inserter 1.

Figure 3A:
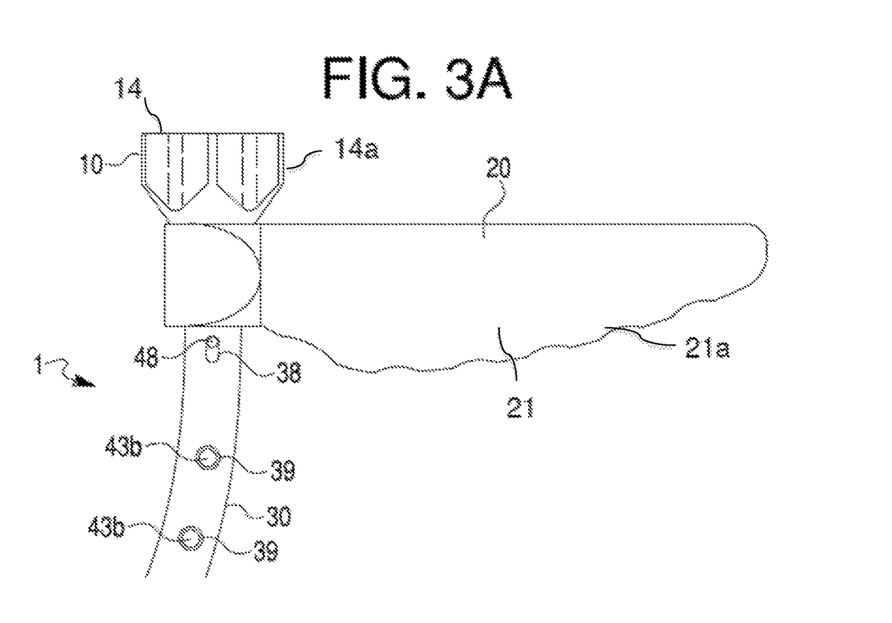
FIG. 3A is a partial perspective view of the proximal portion of the rod inserter of FIG. 1.

FIG. 3A illustrates an embodiment of a handle side (proximal portion) of the rod inserter 1 in accordance with principles of the disclosed subject matter. The handle 20 of the present embodiment can extend approximately perpendicular from the proximal portion of the housing 30 adjacent the knob 10. Additionally, the handle 20 can include a grip portion 21 with contours and indents such that the handle is configured to be gripped by a hand of an operator using the rod inserter 1. The grip portion 21 can have ridges, dimples, rings, collars, or any other configuration of edges and surfaces contoured for gripping. Further, the grip portion 21 can include a cover 21a formed of rubber or another texturized anti-slip material configured to be gripped by the operator using the rod inserter 1.

The present embodiment of FIG. 3A includes the knob 10 disposed at the proximal portion of the rod inserter 1 on a terminating proximal-most end of the housing 30. The knob 10 is configured to rotate relative to the housing 30 to actuate the link structure 40 including the links 43a-c. An exterior portion of the knob 10 may include extensions 14 and texturing 14a so as to be readily gripped for rotating and to provide added leverage and frictional force transferal. The knob 10 may also include apertures 13 extending therethrough to permit cleaning of the knob 10 as well as the link structure 40, housing 30 and adjacent areas. Additionally, the apertures 39 in the housing 30 may expose the links 43a-43b for sanitation purposes, as described above.

The aperture(s) 38 may also expose the guide pin 48 of the link structure 40, which are viewable and/or extend therethrough and are configured to move substantially linearly within the aperture 38 to correspond with movement of the link structure 40 within the housing 30. The aperture(s) 38 can have dimensions such that the guide pin 48 can move a distance within the aperture 38 equal to a distance of movement of the corresponding link 43a, 43b and/or 43c to which the guide pin 48 is attached. Therefore, the dimensions of the aperture 38, and specifically a linear length of an elongated aperture 38, can serve to limit movement of the links 43a-c through the housing 30 by limiting a distance that the guide pin 48 can move within the aperture 38. If the guide pin 48 extends from the links 43a-c, constraints on linear movement of the guide pin 48 (such as a perimeter of the aperture 38) limits movement of the corresponding link 43a-c within the housing 30. In embodiments including multiple guide pins 48 extending from corresponding links, the above described interaction between the guide pins 48 and the apertures 38 may be applicable to each link having a guide pin. In other embodiments, the guide pins may not extend sufficiently through the apertures 38 to limit movement of the links 43a-c. The link 43a and the corresponding guide pin 48 are configured to move linearly as a result of rotational force applied to twist the knob 10, as described below. However, links 43b and 43c (and additional links) can be directed by an interior surface of the opening in the housing 30 to follow the arcuate shape of the housing, and therefore are configured to move in a substantially arcuate manner.

Figure 3B:
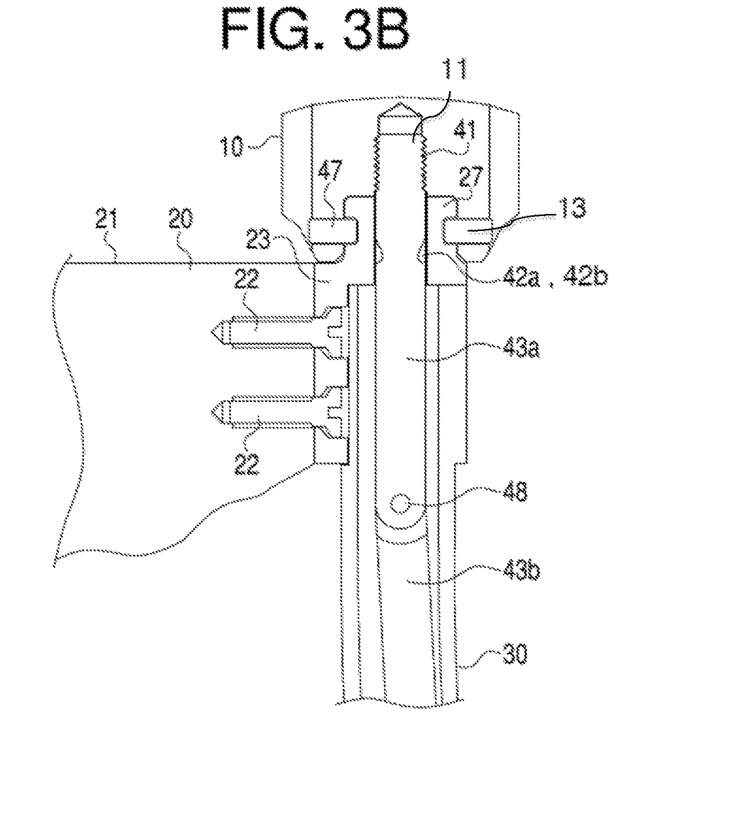
FIG. 3B is a partial cross sectional view of the proximal portion of the rod inserter of FIG. 3A.

FIG. 3B illustrates a cross-section of the proximal portion of the rod inserter 1 in accordance with principles of the disclosed subject matter. The cross-section shows the handle 20 connected to the housing 30 by an attachment end 23 having attachment portions 22 extending therethrough. The attachment portions 22 can be integrated into the attachment end 23, or configured as separate elements inserted through both the attachment end 23 and the grip portion 21 to join them. The attachment end 23 can include a bearing collar 27 that defines a groove configured to position a bearing 47 that will allow the knob 10 to rotate relative to the housing 30 and link structure 40.

In the present embodiment, the proximal end of the housing 30 is joined to the handle 20 at the attachment end 23, the proximal portion of the housing 30 extending substantially perpendicular from a longitudinal axis of the handle 20. The knob 10 is disposed at the terminal end of the housing 30 proximate the handle 20, and is configured to rotate about a longitudinal axis of the housing 30 to linearly move the link 43a, as described below. A bearing 47 can be located between the knob 10 and the housing 30 to facilitate relative rotation between the knob 10 and the housing 30 while allowing the link 43a to move relative to the housing 30 when the knob 10 is rotated. Specifically, the bearing 47 can be held within the bearing groove 27 of the handle 20. The bearing 47 can also be formed as a metal pin that rotates around the groove (including at least 2 pins). The bearing 47 of the present embodiment can be a polyether ether ketone (PEEK) bearing, a roller bearing, and/or other types of bearings, including configurations of rubber, metal, plastic or ceramic may be appropriate for some embodiments. The knob 10 can also include threads 11 disposed within an interior, the threads 11 being configured to engage threads 41 of the link 43a as described below.

The link 43a as shown in FIG. 3B is configured as a threaded inner rod that extends from the interior of the knob 10, through the attachment end 23 of the handle 20, and into the proximal end of the housing 30. The link 43a can be cylindrically shaped, and can have a circular, oval, rectangular, polygonal, or non-symmetrical cross-section taken across its longitudinal axis, or otherwise shaped such that the link 43a can linearly move within the housing 30. A proximal end of the link 43a that extends into the interior of the knob 10 includes the external threads 41 engaged with the internal threads 11 of the interior of knob 10. Rotating the knob 10 thereby rotates the threads 11, which act upon threads 41 of link 43a to motivate the link 43a into or out of the interior by virtue of the threads 41 engagement with the threads 11. Since the knob 10 is not configured for (i.e., is restrained from) movement other than rotation with respect to the housing 30, and is otherwise fixed, screwing the threads 41 of the link 43a results in linear movement of the link 43a within the housing 30. When the cross-section of the link 43a is polygonal, non-symmetrical, or non-circular, the link 43a will abut the housing 30 in such a manner as to resist rotational movement of the link 43a as a result of the screwing motion of the knob 10 described above. Alternatively, the guide pin 48 can extend through the aperture 38 to resist rotational movement of the link 43a (as a result of the screwing motion described above) by abutting the perimeter edges of the aperture 38. Thus, the link 43a can be linearly moved toward the rod side (distal portion) of the rod inserter 1 within the housing 30 as the knob 10 is actuated through rotation of the knob 10.

In the present embodiment, the proximal end of the link 43a can also include an O ring 42b positioned in a seal groove 42a disposed near the bearing 47 of the rod inserter 1. The seal groove 42a and corresponding O-ring 42b can be configured to move linearly with the link 43a.

The guide pin 48, which is inserted through a distal end of the link 43a, is also inserted through a proximate end of the link 43b to thereby join the link 43a with link 43b. Since the links 43a-b have overlapping apertures through which the guide pin 48 is inserted, the guide pin 48 facilitates rotational movement between the links 43a-b while maintaining connection. Therefore, linear movement of the link 43a results in corresponding movement of the connected link 43b (the movement can be a combination of linear movement translated from link 43a to 43b and rotational movement about guide pin 48. As described above, the housing 30 of the present embodiment is curved, and thus the link 43b may also be curved so as to follow the curve of the housing 30 through which it moves. The rotational movement permitted between the links 43a-b by the guide pin 48 further allows the link structure 40 as a whole to follow the curve of the housing 30 as the links 43a-b hinge about the guide pin 48 during movement through the housing 30. A distal end of the link 43b is connected to a proximate end of the link 43c by another guide pin 48, as described below.

Figure 4A:
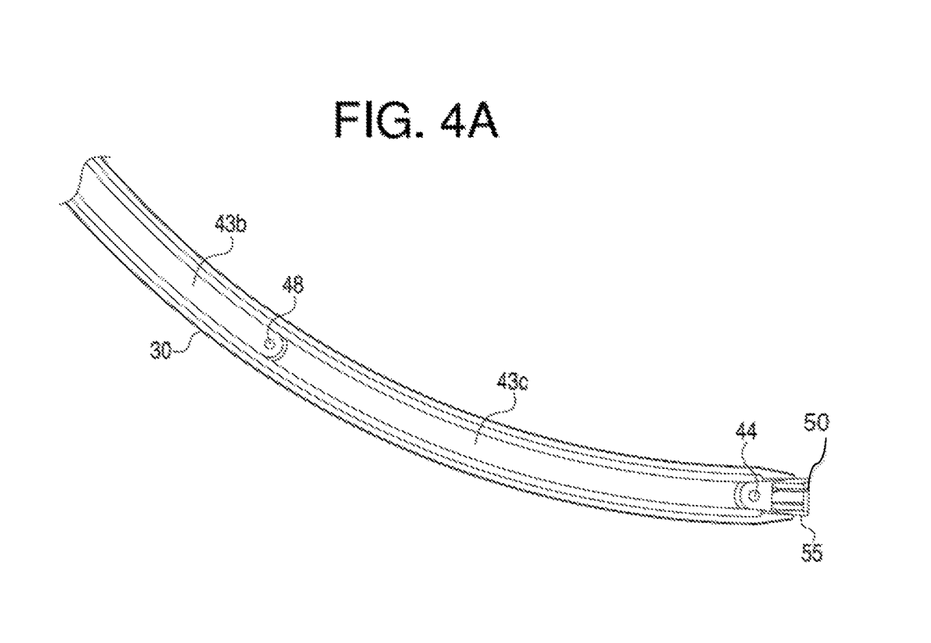
FIG. 4A is a partial cross-sectional view of a distal portion of the rod inserter of FIG. 1.

FIG. 4A illustrates a cross-section of the distal portion of the rod inserter 1 in accordance with principles of the disclosed subject matter. As shown in FIG. 4A, the housing 30 of the present embodiment is curved to facilitate insertion of the rod 92 into the patient. The link 43c can be configured as a lower inner shaft and may also be curved to correspond to the curve of the housing 30. A distal end of the link 43b is shown disposed within the housing 30, the link 43b having the a guide pin 48 inserted therethrough. The guide pin 48 extending through an aperture in the distal end of the link 43b is also inserted through an aperture through a proximate end of the link 43c so as to connect the links 43b-c. The guide pin 48 connects the links 43b-c while permitting rotational movement of the links 43b-c relative to one another as the link structure 40 is moved within the interior of the housing 30. Just as the link 43b is moved within the housing 30 as a result of rotation of the knob 10, the connected link 43c is also moved due to its connection to link 43b. As the link 43c moves along the curve of the housing 30, the links 43b-c can hinge relative to one another to follow the curve.

The rod inserter 1 of the present embodiment can also include a collet 50 configured to clamp the rod 92, as described below. The collet 50 may be connected to a distal end of the link 43c by a guide pin 44 inserted therethrough. The guide pin 48 is inserted through an aperture 56 in the collet 50 so as to permit hinged movement of the collet 50 with respect to the link 43c.

Figure 4B:
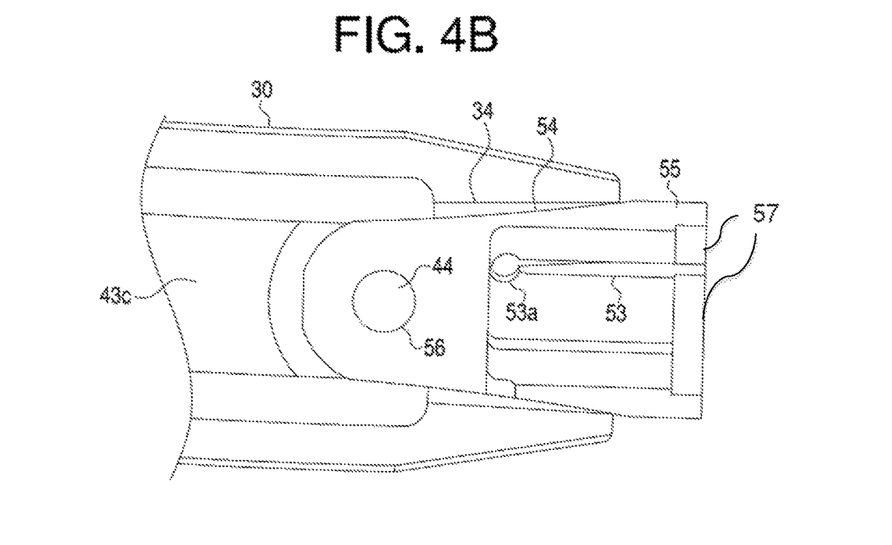
FIG. 4B is a close-up of the partial cross-sectional view of a further distal portion of the rod inserter of FIG. 4A.

FIG. 4B illustrates a cross section of the distal portion of the rod inserter 1 of FIG. 4A in accordance with principles of the disclosed subject matter. The distal portion of the housing 30 is shown surrounding the link structure 40, specifically the link 43c, which in turn is connected to the collet 50. A terminal end of the distal portion of the housing 30 also includes a tapered surface 34, the tapered surface 34 transitioning from a first inner diameter of the housing 30 to a second inner diameter, the second inner diameter being greater than the first. Therefore, an inner diameter of the distal portion widens at the terminal end. In the present embodiment, the tapered surface 34 of the terminal end substantially corresponds to a tapered surface 54 of the collet 50, with the tapered surface 54 widening in accordance with the tapered surface 34. The tapered surfaces 34,54 are tapered at approximately corresponding angles, however their angles of taper may vary to a degree so as to avoid taper lock characteristics.

The collet 50 of the present embodiment is formed with the tapered surface 54, and is disposed adjacent and can extend beyond the terminal end of the housing 30. The tapered surface 34 is thereby configured to compress or release the tapered surface 54 of the collet 50 as the link structure 40 is moved linearly within the housing 30. Compression of the tapered surface 54 of the collet 50 squeezes a split portion 53 of the collet 50 together, the split portion 53 being hinged about a split end 53a. The split portion 53 can extend from an intermediate portion of the collet 50 through to a distal end 55. The above described configuration of the collet 50 allows the rod inserter 1 to clamp onto the rod 92 and thereby secure the rod 92 for insertion into the patient, which is described in more detail below.

As described above, the collet 50 is disposed within the distal portion of the housing 30. The collet 50 of the present embodiment is shown as a one piece structure with splits that allow the collet 50 to spring closed and opened (i.e., allows a diameter of the collet 50 to reduce or become larger) under force of the surface 34 against surface 54 that occurs during withdrawal of link structure 40 (and attached collet 50) into the housing 30. However, the collet 50 does not have to be a single piece construction, and instead can include top and bottom portions that are either hinged to each other or attached in a way that allows relative movement therebetween. Each of the top and bottom portions may include respective halves of an aperture 56, such that cross sections of the respective halves of the aperture 56 are approximately symmetrical. Alternatively, the split portion 53 may divide the collet 50 into asymmetrical top and bottom portions configured to clamp onto and secure the rod 92. The split portion 53 can be made up in halves, thirds, or quarters (or other) and shaped like a pie. As described above, the split portion 53 can also include the split end 53a configured to join the top and bottom portions and serve as the hinge when the collet 50 clamps onto the rod 92. The split end 53a may be configured as a living hinge, or may alternatively be configured as any other appropriate type of hinge. The split portion 53 is configured to cause the top and bottom portions of the collet 50 to move in a substantially linear motion towards and away (together and apart) as a result of being compressed and released by interaction of the tapered surfaces 54, 34 of the collet 50 and housing 30, respectively during actuation. Although, it should be noted that the motion of the top and bottom portions of the collet 50 can strictly be considered to be rotational. Thus, the substantially linear motion should be considered to include this type of rotational motion (having a relatively large center of rotation) between the top and bottom portions of the collet 50 such that, in effect, the top and bottom portions basically move toward and away from each other. The collet 50 of the present embodiment has a spring back bias such that opposing sides of the collet 50 can return to a pre-compressed state when the link structure 40 is moved away from the handle 20 by virtue of rotating the knob 10. Clamping and release of the rod 92 is thereby dependent upon corresponding motion of opposing sides of the collet 50, and specifically, release of the rod 92 from the collet 50 may be dependent upon spring back of the collet 50.

In the present embodiment, the knob 10 has interior threads 11 to engage the threads 41 of the link structure 40. The link structure 40 can therefore be moved along the housing 30 through rotation of the knob 10, which effectively screws the link 43a of the link structure 40 along the threads 41. If the knob 10 is rotated so as to move the link structure 40 towards the proximate portion of the housing 30, the tapered surface 34 of the housing 30 contacts the taper surface 54 of the collet 50 and causes the collet to clamp together about the split end 53a so as to narrow a gap in the split portion 53. When contacted and compressed, clamping arms 57 of the collet 50 move towards each other while also being able to rotate together about the split end 53a, thus clamping the arms 57 of the collet 50 together to cause a reduction in an inner diameter of the collet 50 (or narrowing or sandwiching of an opening, if only a top and bottom arm 57 are present). Clamping the collet 50 can secure an end of the rod 92 within the collet 50 and facilitate insertion of the rod 92 into the patient. The collet 50 of the present embodiment could be configured to prevent axial roll of the rod 92 and may include a hex-shaped or otherwise polygonal aperture, especially with use of a rod having a hex-shaped or polygonal connection end. In some embodiments, geometry of the aperture 56 in the collet 50 and an engageable end of the rod 92 may be varied so as not to be hex-like or polygonal, yet still able to prevent roll, such as by being elliptical. Furthermore, some embodiments may include additional aperture geometry and corresponding rod end geometry to increase axial force required to pull-out the rod, for example, a lip and annular groove structure could be provided to enhance axial locking if desired.

FIGS. 2A-D illustrate an exemplary method of use of the rod inserter 1 at various stages of insertion of the rod 92 into the patient (and, for example, into pedicle screws 93). As shown in FIGS. 2A-D, downtubes 94 are attached to the screws 93 such that a portion of each downtube 94 is inserted within the patient, while another portion remains outside of the patient. The downtubes 94 can be removably attached to the screws 93 by any appropriate method including screwing, clamping, etc. In addition, at the beginning of the procedure depicted in FIGS. 2A-D, a user (such as an orthopedic surgeon, nurse, or technician) can attach the rod 92 (that is to ultimately be inserted into and locked into the pedicle screws 93 in the patient) to the rod inserter 1 by placing a proximal end 921 of the rod 92 into collet 50. Once located in the collet 50, the user can actuate an actuation device (e.g., can rotate knob 10), to cause the collet 50 to be withdrawn into housing 30 which, in turn, causes the collet 50 or other lock structure to connect and lock to the rod 92. If the proximal end 921 of the rod is non-symmetrical, the rod 92 can be securely attached at the distal-most end of the rod inserter in a locked configuration such that the rod 92 cannot be either withdrawn from or rotated with respect to the collet 50 (and rod inserter 1). Thus, in this state, the user can then take the initial step of inserting the rod 92 into a patient once an incision is made at a predetermined location spaced from the target screw 93. The curvature of the housing 30 can be configured to provide the most beneficial entry location for the rod 92 into the patient such that a user can easily persuade the rod 92 both initially into the patient and then into the downtube(s) 93 and pedicle screw(s) 93 by minimal force and using a minimal incision and insertion track.

The exemplary pedicle screws 93 may be polyaxial or monoaxial screws configured for use in the spine for stabilization in spine fixation, particularly bony fusion. Alternatively, the screws 93 may be configured as anchor points for a dynamic system. To create the anchor points with the screws 93, the screws 93 can be inserted into bone through pedicles of the respective vertebrae. Each screw 93 may include threads, a receiver structure that includes a throughway for insertion of the rod 92, as well as internal threads and a set screw located at a top portion of the throughway for securing the rod 92 in place after insertion. Insertion of the screws 93 into a patient can be through a posterior approach, for example, to the thoraco-lumbar spine, such that the threads can be screwed into vertebrae of the patient. The internal threads can be configured to receive the respective set screw to secure the rod 92 within the throughway. The throughway or received structure of the pedicle screw 93 can be configured as a saddle or U-shaped aperture so as to accommodate insertion of the rod 92.

In the present embodiment, the screws 93 can be initially screwed into vertebrae of the patient. The screws 93 may be screwed into adjacent or consecutive vertebrae, however other combinations of vertebrae may be joined via screws 93 and insertion of the rod 92. With the screws 93 properly positioned in the vertebrae, the rod 92 can be inserted through the receiver structure throughways of the respective screws 93. Based on the disposition of the vertebrae and screws, the rod 92 may be curved or bowed to be more readily insertable into the throughways, however, the rod 92 may also otherwise be straight. To secure the rod 92 once it has been inserted into the receiving structure throughways, the set screws may be screwed into the internal threads of the respective screws 93 and/or rod persuader tools can be used to set the rod 92 in place via the upper aperture (when the set screw is not yet in place) in the receiving structure of the screw(s) 93. Once the rod is properly located in the saddle or U-shaped aperture (receiving structure) of the screw 93, rotating/threading the set screw compresses the rod 92 into the receiving structure to lock down the rod 92 and secure it against movement of the vertebrae or screw(s) 93. Once secured, the rod 92 can serve as a rigid bridge between the screws 93 configured as anchors in the vertebrae. The exemplary rod 92 in FIGS. 2A-D is shown connecting a pair of vertebrae via the screws 93, however the rod inserter 1 may be configured to insert a rod 92 for connecting any number of vertebrae via respective screws, such as one, two, three, four, five, etc.

Figure 2A:
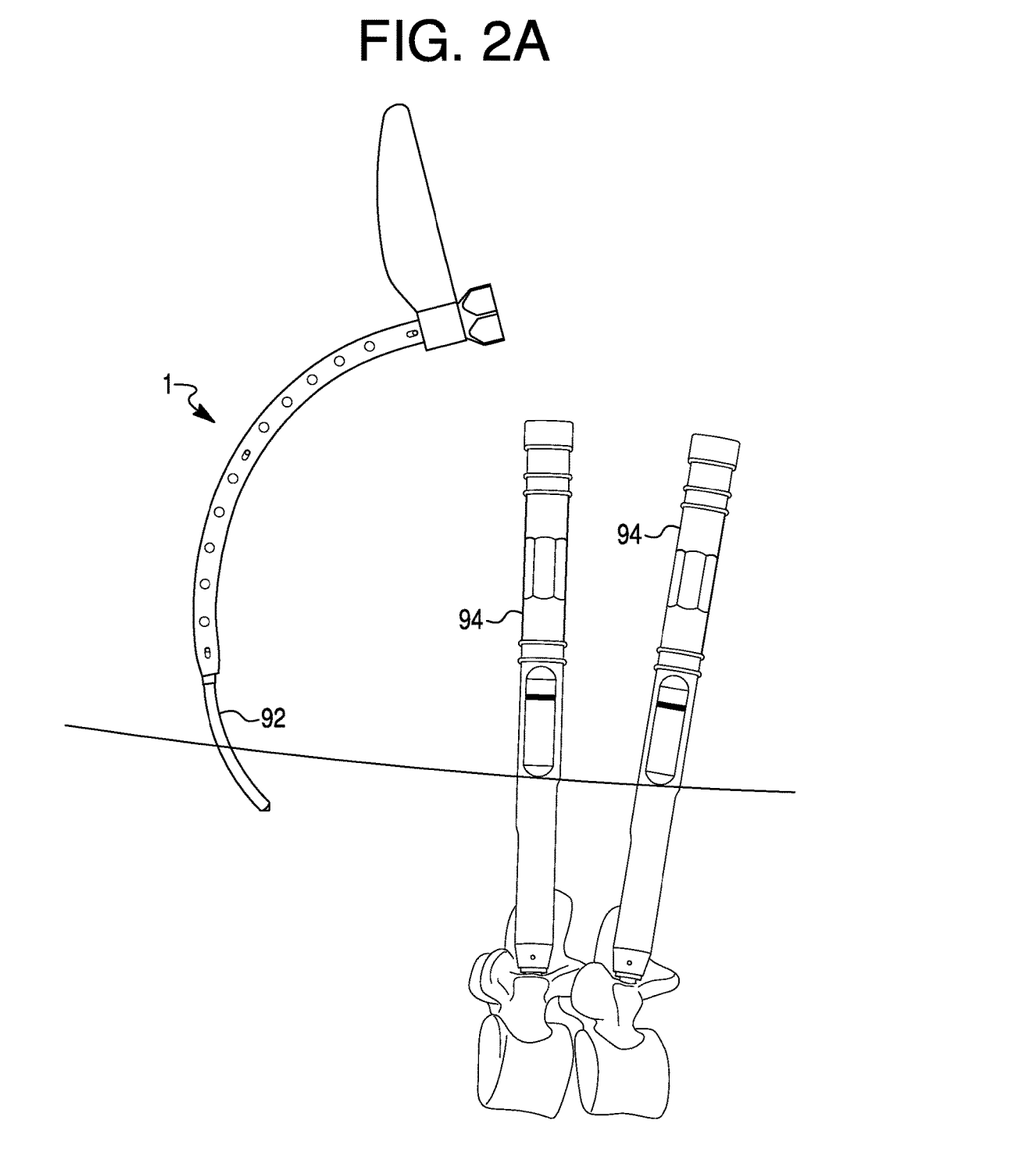
FIG. 2A is a perspective view of the rod inserter of FIG. 1 depicting a method of using the rod inserter.

In FIG. 2A, the downtubes 94 are shown inserted into incision wounds of the patient and attached to the screws 93, wherein the screws 93 are attached to the vertebrae of the patient. The rod 92, shown attached to the rod inserter 1, is held in an angled orientation so as to be insertable into another minimally invasive wound in the patient spaced from the wounds into which the respective downtubes 94 have been inserted. To maintain angled insertion of the rod 92, the rod inserter 1 is held at the handle 20 by the operator such that the curve of the rod inserter 1 yields an appropriate angle of insertion into the wound.

Figure 2B:
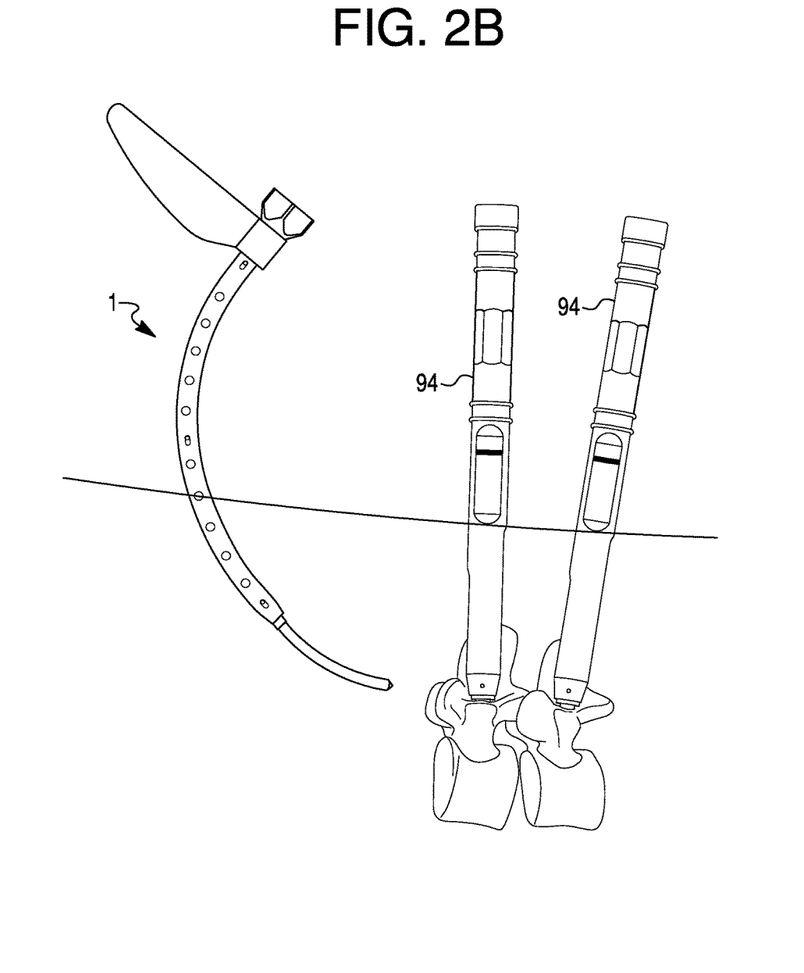
FIG. 2B is a perspective view of the rod inserter of FIG. 1 depicting a method of using the rod inserter.

In FIG. 2B, the rod 92 and rod inserter 1 are shown pushed into an initial insertion into the patient. As the rod 92 is pushed further into the patient, the operator pushes the rod inserter 1 along a path of the curved housing 30 through the wound. This curved path of insertion allows the rod 92 to approach an approximately horizontal insertion direction within the patient when the rod 92 reaches the first downtube 94. Each downtube 94 may have a longer side slot opposing a shorter side slot, wherein the first downtube 94 is oriented such that the rod 92 can be initially pushed into insertion within the longer side slot.

Figure 2C:
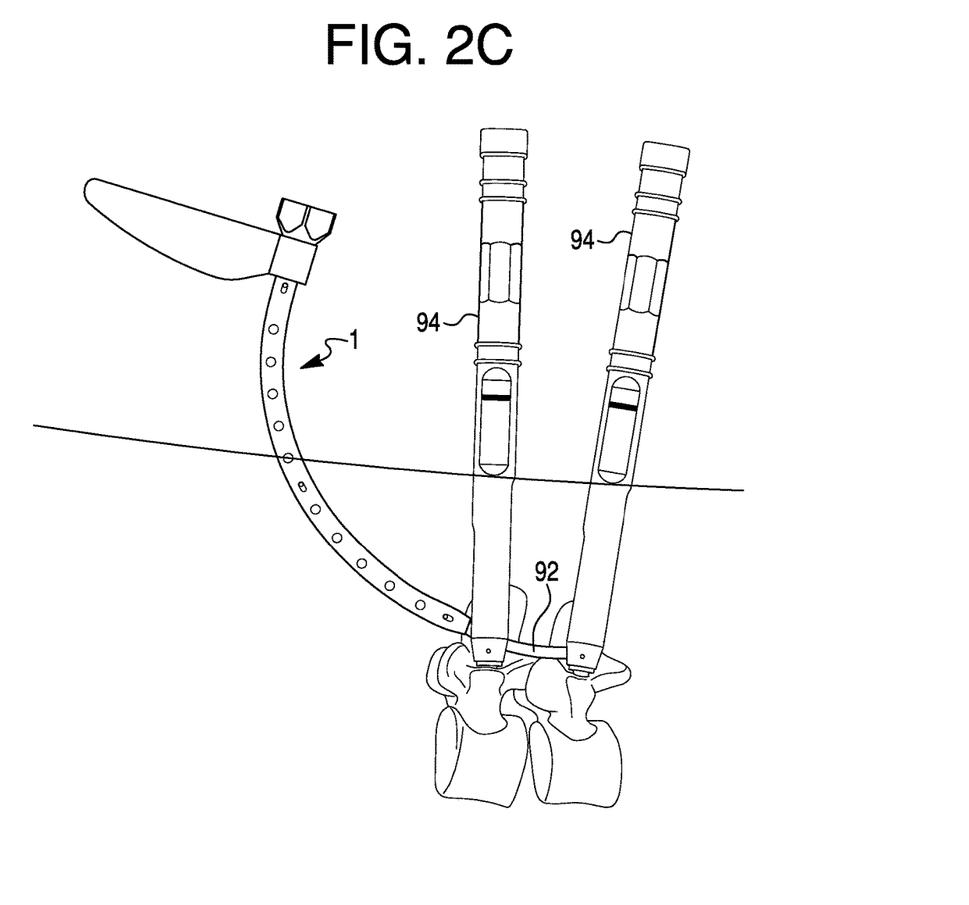
FIG. 2C is a perspective view of the rod inserter of FIG. 1 depicting a method of using the rod inserter.

In FIG. 2C, the rod 92 is shown having passed through both of the downtubes 94 in a near horizontal orientation (or perpendicular orientation with respect to a longitudinal axis of each of the downtubes 94). This is due to the angle of insertion through the wound for the rod 92 and rod inserter 1, and the curve of the rod inserter 1. In the present embodiment, the curve of the rod inserter 1 can define a trajectory for the rod 92 to follow into the patient and through the downtubes 94, by which stage the rod 92 is approximately horizontal and the handle 20 of the rod inserter 1 can be approximately parallel to the operating surface of the patient. In some embodiments, depending on length and curvature of the rod inserter 1, the handle 20 may not be approximately parallel to the operating surface of the patient when the rod 92 has been fully inserted through the downtubes 94 and pedicle screws 93. The rod 92 can be inserted into the adjacent downtube 94 through the respective slot such that the rod 92 extends through both of the downtubes 94 and through the reception structures of the heads of each of the pedicle screws 93.

Figure 2D:
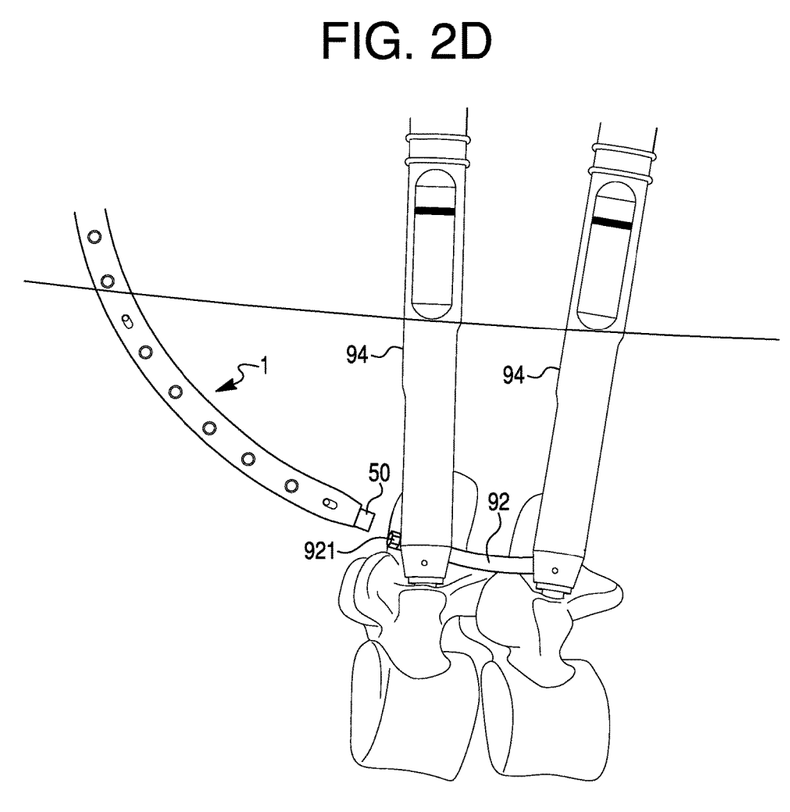
FIG. 2D is a perspective view of the rod inserter of FIG. 1 depicting a method of using the rod inserter.

In FIG. 2D, the rod 92 has been released from the rod inserter 1. This is accomplished by first ensuring the rod 92 is in place within the pedicle screw 93 (i.e., set screws and/or rod persuaders can be used in conjunction with the downtubes 94 according to user preference in order to secure the rod 92 is in place and secure in the pedicle screws 93). Once the rod 92 is in place and/or secured, the user of the rod persuader can de-actuate the actuation structure (e.g., can rotate the knob 10 in a counter clockwise direction) to cause the rod connection structure (e.g., collet 50) to de-couple from the rod 92. Once released, the rod inserter 1 can be moved away from the rod 92. As shown in FIG. 2D, the rod 92 is decoupled from inserter 1 and the rod end geometry 921 of the rod 92 can be viewed. In this embodiment, the rod end geometry 921 is formed as a hexagon shape. Once decoupled, the rod inserter 1 can be removed from the patient through the wound while the rod 92 remains inserted through both downtubes 94 in a near horizontal orientation to bridge the screws 93 and join them together.

In the disclosed embodiment, various rod inserter structures are applied to an instrument for insertion of a rod that joins pedicle screws fixed to a patient's vertebrae. However, the disclosed structures may alternatively be applied to or modified to cover any type of instrument configured to manipulate medical implants, including implantation of any rod structure for location adjacent a bone.

In the disclosed exemplary embodiments, the rod inserter 1 is configured for use by operators having different dominant body sides, such as right-handed and left-handed operators. Embodiments are also intended to include or otherwise cover methods of using and methods of manufacturing any or all of the elements disclosed above. The methods of manufacturing include or otherwise cover processors and computer programs implemented by processors used to design various elements of the rod inserter disclosed above.

While the subject matter has been described in detail with reference to exemplary embodiments thereof, it will be apparent to one skilled in the art that various changes can be made, and equivalents employed, without departing from the scope of the invention. For example, the number of various components can be changed without departing from the scope and spirit of the disclosed subject matter. Specifically, the link structure 40 can include multiple shafts linked together to ensure appropriate length and shape, including greater or fewer number of links than the three links 43a-b shown in the accompanying drawings. The collet 50 can be a single piece structure that has flexible arms 57 that spring inward to reduce the aperture opening of the collet, or can be multiple structures that are hinged together via a separate hinge structure such as a living hinge, or a hinge that also includes several structures, such as guide structures and pin(s). In addition, the aperture 56 of the collet 50 can be various shapes and fall within the spirit of the presently disclosed subject matter. For example, the aperture 56 can be circular, non-symmetrical, elliptical, oblong, polygonal, hexagonal, or various other shapes that are configured to mate with an associated end of the rod 92. The aperture 56 can also include lips and annular rings and other structures located therein to assist in guiding, location and connection of the rod 92 with the aperture 56 in the collet 50.

A reversal of parts for the disclosed mating structures is also contemplated to be within the scope of the presently disclosed subject matter. For example, the threads of each of the threaded structures can be placed at different locations and on different structures to effect the same or similar motion for locking the rod 92 within the collet 50. In addition, the location of specific structures can be reversed, for example, the knob 10 could be located at an intermediate portion of the housing 30.

The manner in which movement between each of the structures is facilitated can also be changed. For example, the bearing that facilitates rotational movement between the knob 10 and the housing 30 can have multiple configurations that permit or facilitate such rotational movement, such as, for example, ball bearings, fluid bearings, tapered bearings, frictional surface bearings, and other known bearing structures or configurations, or no bearing. Also, the knob 10 could be replaced with a lever or other structure that actuates the collet or other rod connection structure. Likewise, the rod connection structure can be formed other than a collet 50, such as a vice grip type locking mechanism or other hinged mechanism, or other aperture reducing apparatus.

Although the rod inserter 1 is disclosed as having a central opening extending along the entire length of the housing 30 to facilitate relative movement of the link structure 40, the rod inserter 1 could be provided without such a central opening and could rely on links that are configured as plates or other structures that run linearly adjacent the housing of the device and not coincident with the longitudinal axis of the housing. In addition, the cross-sectional shape of the housing 30 taken perpendicular to the longitudinal axis of the housing 30 is shown as substantially rectangular with the opening running through the inner extent of the rectangular shape. However, this cross-section shape can be different and fall within the scope of the disclosed subject matter. For example, the cross-section shape can be circular, oval, polygonal, oblong or non-symmetrical. In addition, the cross-sectional shape can change along the length of the housing 30 for various reasons, for example, to provide guideways for the links 43a-c at certain locations along the length of the housing 30.

The various structures of the rod inserter 1 can each be assembled from multiple parts and formed of different materials, or can each be constructed as a single homogeneous body of material, rather than an assembly of parts. In addition, the material can be a biocompatible material and/or antimicrobial. Suitable materials include but are not limited to stainless steel, titanium, other metals, metal alloys, ceramics, plastics, or superelastic shape memory alloys like Nitinol, or combinations thereof. Actuation mechanisms such as the knob 10 can be made from a plastic material to reduce the weight of the rod inserter 1, but can just as likely be made from stainless steel, titanium, other metals, metal alloys, ceramics, other plastics, or superelastic shape memory alloys like Nitinol, or combinations thereof. In addition, the spinal rod 92 and/or collet 50 can include a magnetic material to facilitate connection therebetween.

While the method of use of the rod inserter 1 and system is described in a chronological series of steps, the steps of the method need not be chronological. Instead, certain actions can occur simultaneously or in reverse or different order while remaining within the scope of the presently disclosed subject matter. Additional or different intervening steps can also be included in the method, and/or certain steps and functions can be omitted.

If the link structure 40 were fitted with a lever instead of a knob for actuation, the link structure 40 could be motivated to return to its non-actuated, non-locking position through use of various structures, such as a simple spring biased return, a magnetic return, a pneumatic return, or other return structure.

The longitudinal axis is an axis that extends along a longest extent of a structure. The longest extent can be along a straight line and can also be along a curved line, or combination thereof. In addition, it should be noted that the term substantially as used herein describes a structure that is exactly at or almost at the specified parameter to the extent one of ordinary skill in the art would appreciate.

Although the method and structures are described for use in a minimally invasive surgery (MIS) technique, the disclosed embodiments could be used in open surgery and/or combinations of MIS and open surgery.

While the subject matter has been described in detail with reference to exemplary embodiments thereof, it will be apparent to one skilled in the art that various changes can be made, and equivalents employed, without departing from the scope of the invention. All related art references discussed in the above Description of the Related Art section are hereby incorporated by reference in their entirety.

What is claimed is:

1. A rod inserter for use with a rod, comprising:
   a handle;
   a curved extension structure extending from the handle, the extension structure having a distal end, a proximal end, and a longitudinal axis, the extension structure including a passageway extending along the longitudinal axis of the extension structure;
   a rod connection structure located at the distal end of the extension structure, the rod connection structure being disposed within the passageway and encompassed by the extension structure, the rod connection structure configured to connect and disconnect from the rod;
   a proximal linkage structure located in the passageway of the extension structure and adjacent the handle; and
   a distal linkage structure located in the passageway of the extension structure and connected to the rod connection structure by a guide pin which permits hinged movement of the entire rod connection structure with respect to the distal linkage structure, wherein the proximal linkage structure is connected to the distal linkage structure, and the distal linkage structure is configured to cause the rod connection structure to connect to the rod when the distal linkage structure is moved in a first direction, and to cause the rod connection structure to disconnect from the rod when the distal linkage structure is moved in a second direction substantially opposite to the first direction.

2. The rod inserter of claim 1, wherein the distal linkage structure is curved.

3. The rod inserter of claim 2, further comprising:
an intermediary linkage structure disposed between the proximal linkage structure and the distal linkage structure.

4. The rod inserter of claim 3, wherein the intermediary linkage structure is curved.

5. The rod inserter of claim 4, wherein the proximal linkage structure is connected to the intermediary linkage structure by an intermediary pin, and the distal linkage structure is connected to the intermediary linkage structure by a distal pin.

6. The rod inserter of claim 5, wherein the extension structure includes at least one window portion located adjacent one of the intermediary pin and the distal pin such that movement of the one of the intermediary pin and the distal pin during actuation of the rod inserter is viewable from a location external to the rod inserter.

7. The rod inserter of claim 6, wherein the extension structure includes indicia located adjacent the at least one window portion designating at least one of a locked and an unlocked position.

8. The rod inserter of claim 1, further comprising:
an actuation structure located adjacent the handle and configured to move the distal linkage structure in the first direction when actuated and to move the distal linkage structure in the second direction, which is different from the first direction, when de-actuated, such that the rod connection structure connects to the rod when the actuation structure is actuated, and such that the rod connection structure disconnects from the rod when the actuation structure is de-actuated.

9. The rod inserter of claim 8, wherein
the actuation structure is a knob that includes internal threads, and the proximal linkage includes external threads that threadably engage with the internal threads of the knob, and actuation of the actuation structure is accomplished by rotation of the knob in a first rotary direction causing the proximal linkage to move in a linear direction with respect to the knob.

10. The rod inserter of claim 1, wherein the rod connection structure includes a collet attached to the distal linkage structure.

11. The rod inserter of claim 10, wherein the passageway includes a tapered inner surface, the tapered inner surface slidingly engages with an exterior surface of the collet wherein the collet flexes inwardly towards the longitudinal axis of the extension structure when the collet is drawn into the passageway by the distal linkage structure.

12. A rod inserter, comprising:
a handle;
an arcuate housing extending from the handle, the housing defining a passageway extending along a longitudinal axis of the housing;
a plurality of links located in the passageway of the housing, at least one of the links extending in an arcuate manner along the longitudinal axis of the housing;
a rod connection structure disposed within the passageway and encompassed by the housing, wherein the rod connection structure is connected to at least one of the plurality of links by a guide pin which permits hinged movement of the entire rod connection structure with respect to the at least one of the plurality of links, and wherein the rod connection structure is configured to connect to and release from a rod; and
an actuation structure connected via the plurality of links to the rod connection structure, the actuation structure configured such that actuation of the actuation structure causes the rod connection structure to connect to the rod and de-actuation of the actuation structure causes the rod connection structure to release from the rod.

13. The rod inserter of claim 12, wherein the actuation structure is a knob configured to rotate about the longitudinal axis of the housing, and the knob includes internal threads, and at least one of the plurality of links includes external threads that threadably engage with the internal threads of the knob, and rotation of the knob in a first rotary direction moves the plurality of links with respect to the housing.

14. The rod inserter of claim 12, wherein the actuation structure is a knob that includes internal threads, and a proximal one of the plurality of links includes external threads that threadably engage with the internal threads of the knob, and actuation of the actuation structure is accomplished by rotation of the knob in a first rotary direction causing the proximal one of the plurality of links to move in a linear direction with respect to the knob.

15. The rod inserter of claim 12, wherein the actuation structure is configured such that actuation of the actuation structure moves at least one of the plurality of links along the longitudinal axis of the housing.

16. The rod inserter of claim 12, wherein the rod connection structure includes a collet structure located at a distal end of the plurality of links.

17. The rod inserter of claim 16, wherein the housing includes a tapered surface located inside a distal end of the passageway, the tapered surface slidably engages with an exterior surface of the collet wherein the collet flexes inwardly towards the longitudinal axis of the housing when the collet is drawn into the housing by a distal one of the plurality of links.

18. The rod inserter of claim 12, wherein each of the plurality of links is connected to an adjacent one of the plurality of links by a pin.

19. The rod inserter of claim 18, wherein the housing includes at least one window portion located adjacent the pin such that movement of the pin during actuation of the rod inserter is viewable from location external to the rod inserter.

20. The rod inserter of claim 19, wherein the housing includes indicia located adjacent the at least one window portion designating at least one of a locked and an unlocked position.

21. A method of using a rod inserter for inserting a rod, comprising:
providing a rod inserter including,
a handle,
an actuator located adjacent the handle,
an extension structure extending from the handle, the extension structure having a distal end, and a proximal end, the extension structure including an passageway running along and defining a curved longitudinal axis of the extension structure,
a plurality of links located in the passageway of the extension structure, and
a rod connection structure located at the distal end of the extension structure, the rod connection structure being disposed within the passageway and encompassed by the extension structure, the rod connection structure configured to connect to and release from the rod, the rod connection structure being connected to one link of the plurality of links by a guide pin which permits hinged movement of the entire rod connection structure with respect to the one link of the plurality of links;

actuating the actuator to move at least two of the plurality of links along the curved longitudinal axis of the extension structure; and actuating the actuator to cause the rod connection structure to one of connect to the rod and release from the rod.

* * * * *